United States Patent [19]

Lubeck et al.

[11] Patent Number: 5,100,390
[45] Date of Patent: Mar. 31, 1992

[54] LUBECK SPINAL CATHETER NEEDLE

[75] Inventors: Norma A. Lubeck, 4137 Heather Rd., Long Beach, Calif. 90808-1625; Roberta C. Butler, Auburn, Calif.

[73] Assignee: Norma A. Lubeck, Long Beach, Calif.

[21] Appl. No.: 602,205

[22] Filed: Oct. 22, 1990

[51] Int. Cl.$^5$ .............................................. A61M 5/00
[52] U.S. Cl. .................................... 604/158; 604/274
[58] Field of Search ............... 604/158, 160, 187, 239, 604/264, 272-274; 606/223

[56] References Cited

U.S. PATENT DOCUMENTS

| 2,634,726 | 4/1953 | Hanson | 604/274 |
|---|---|---|---|
| 2,922,420 | 1/1960 | Cheng | 604/158 |
| 4,518,383 | 5/1985 | Evans | 604/272 |
| 4,650,472 | 3/1987 | Bates | 604/158 |
| 4,685,904 | 8/1987 | Krebs | 604/239 |
| 4,721,506 | 1/1988 | Teves | 604/158 |
| 4,795,446 | 1/1989 | Fecht | 604/239 |
| 4,808,157 | 2/1989 | Coombs | 604/272 |
| 4,842,585 | 6/1989 | Witt | 604/274 |
| 4,958,901 | 9/1990 | Coombs | 604/158 |
| 4,994,036 | 2/1991 | Biscoping et al. | 604/158 |

FOREIGN PATENT DOCUMENTS

| 3020926 | 12/1981 | Fed. Rep. of Germany | 604/274 |
|---|---|---|---|
| 9001349 | 2/1990 | PCT Int'l Appl. | 604/272 |

Primary Examiner—C. Fred Rosenbaum
Assistant Examiner—Chalin Smith

[57] ABSTRACT

A needle hereafter referred to as a metal cannula is of thin-walled construction and designed with a solid non-cutting pencil point possessing a tip with an elliptical side port located not more than 1 (one) cannula Outer Diameter (O.D.) length from the tip and via a hollow internal channel the axial length of the cannula is capable of guiding an inserted catheter through the cannula for projection laterally out of the cannula for subsequent indwelling placement of the introduced catheter upon removal of the cannula. The sideport is placed on the angled surface of the developing point so that it coincides with the angle of the pencil point. The elliptical sideport has a machined and polished rounded internal edge intersecting with the external surface. The construction of the cannula combining a large diameter with a pencil point and the location of an opening at the tip permits safe introduction of a spinal catheter into the subarachnoid space with minimum damage to tissues or membranes by either the cannula or a catheter exiting the sideport. The cannula is fitted with an obturator which coincides with the shape of the internal lumen of the cannula where the obturator tip curves upward to occlude the opening of the cannula sideport. The cannula of the present invention has application to subarachnoid and epidural regional anesthesia and pain management procedures. The present invention is designed preferably as a large gauge needle (17-21 gauge) so that it will accept insertion of a large flexible catheter (20 to 22 gauge in diameter) for indwelling placement.

7 Claims, 6 Drawing Sheets

LUBECK SPINAL CATHETER NEEDLE

BACKGROUND OF THE INVENTION

1. Field of the Invention

The present invention relates to a metal cannula with a lumen (medical tube device) for insertion by percutaneous puncture to provide spinal and epidural anesthesia and pain management earlier described in Disclosure Document No. 263349 dated 20 SEP 90.

2. Description of Related Art

Spinal catheters are commonly placed intrathecally via a cannula. The cannula being introduced percutaneously and advanced to penetrate the dural membrane of the spinal column. Subsequently, a spinal catheter is introduced through the lumen of the cannula followed by removal of the cannula and indwelling retention of the catheter in the subarachnoid space. Medical and anesthetics are introduced through the indwelling catheter for effect. The indwelling catheters remain in place for extended periods to permit the injection of anesthetics or medicine as needed.

Cannula devices have been designed to minimize trauma associated with percutaneous insertion. Tip geometry has been shown to impact severity of the rent damage (cutting or tearing) to underlying vascular and neural structures and the dural membrane. Needle tip gauge has been shown to impact the size of the rent caused by the cannula. Both the size of rent AND the severity of rent are associated with complications of dural puncture: 1) vascular, neural and dural puncture membrane trauma; 2) post-dural puncture headache; 3) hematoma formation in the epidural and subarachnoid spaces; 4) paraesthesia and functional loss of nerves/neurons. Logically, pencil pointed cannula tip geometry suggests the most atraumatic design for penetration of the dural membrane fibers and avoidance of cutting of vascular and neural structures by sharp pointed cutting tip needles of the Pitkin or Quincke type (Bates, U.S. Pat. No. 4,650,472). A cannula diameter of less than 25 gauge suggests the maximal size of a sharp point beveled cannula which can penetrate the dura while maintaining a very low incidence of post dural puncture headache as opposed to traditionally large diameter needles (17 to 19 gauge) of the Hustead or Touhy tip design which are intentionally employed for administration of epidural anesthesia (Coombs, U.S. Pat. No. 4,808,157; Evans, U.S. Pat. No. 4,518,383; Cheng, U.S. Pat. No. 2,922,420).

At present, catheters specifically designed for insertion into the subarachnoid space have a diameter compatible with insertion into traditional sharp cutting tip geometry spinal cannulas (Quincke and Pitkin types) (also U.S. Pat. No. 4,994,036). These cannula are typically 25 gauge or of smaller diameter and permit introduction of a smaller diameter gauge catheter through the cannula into the subarachnoid space. Thus in order to lower the incidence of a post dural puncture headache complication associated with puncture and/or cannulation of the dural membrane, operators have traditionally employed very small diameter cannula. Small catheters are difficult to thread through the small cannula channel and accurately place in the subarachnoid space. The 32 gauge catheters currently used quickly heat to body temperature and become excessively pliable. This thwarts accurate catheter insertion and promotes knotting and kinking of the catheter in the subarachnoid space. Additionally, the small diameter of the 32 gauge catheter encourages its penetration of neural and vascular structures both upon introduction of the catheter (especially when a stylette is used to stiffen the catheter) and by migration of the indwelling catheter.

There is known a catheter set for spinal anesthesia that allows placement of a "thick spinal catheter" by threading over a guidewire previously introduced through a sharp pointed spinal needle which itself has been threaded through a sharp pointed cannula placed into the epidural space (Biscoping et al, U.S. Pat. No. 4,994,036). The main disadvantages with the invention and the process of it application are the following: 1) the sharp flat inclined tip "epidural" cannula may inadvertently puncture the dura especially since its application requires several additional manipulations associated with subarachnoid space catheter placement (threading of a spinal cannula, threading of a guidewire, threading of a catheter), and 2) accurate guidewire introduction into the subarachnoid space cannot be evaluated until the spinal cannula-guidewire assembly is removed and the cannula threaded into place. Thus the cannula could be threaded over a guidewire that was inadvertently introduced into a neural or vascular structure or even exit entirely from the subarachnoid space. This would compound the trauma to these structures and require another maneuver to attempt cannula-guidewire-catheter placement. Finally, the sharp pointed beveled tip geometry of the spinal cannula introduced through the epidural cannula acts as a cutting surface. This cutting action is traumatic to the dural membrane and underlying structures. Additionally, the cutting surface may shear either the guidewire or the spinal catheter during the application procedure.

It is known that long beveled needles used for spinal anesthesia such as the Quincke and Pitkin spinal needles can bend away from the beveled surface as the needle tip travels through the tissues. This deflection is significantly reduced if the needle possesses pencil point tip geometry.

It is also known that large gauge (22 gauge or greater diameter) spinal needles have an advantage over smaller diameter needles because a larger gauge provides better tactile and proprioceptive feedback to the operator as the needle tip is advanced through the tissues of the back during application. In addition, because the 22 gauge or larger diameter needle is more rigid, it can be more easily and accurately directed to the target site without undetected deflection of the tip.

SUMMARY OF THE INVENTION

It is the principle object of this invention to improve upon the Witt needle (U.S. Pat. No. 4,842,585) construction, or any others, not currently known, employing this metal cannula construction.

Thus, it is the object of the invention to provide a cannula for introduction into the subarachnoid space which minimizes cutting and/or tearing damage to the nerves, blood vessels and dural membrane through the use of a needle tip geometry of pencil point design, but the major surface angle of which is inclined enough to prevent "blunt" tip trauma to penetrated tissues.

It is a further object of this invention to prevent the formation of fish-hooks at the tip of the cannula which result after a sharp needle point (example: Quincke or Pitkin tipped needles) encounters calcified or fibrous tissue or bone. The re-introduction of the fish-hooked tip into the soft tissues can cause further tissue trauma.

It is a further object of the invention to provide a cannula for introduction into the subarachnoid space which minimizes damage and/or penetration of structures immediately beneath the dura by locating the sideport opening of the cannula as close to the tip of the cannula as possible, thereby reducing the distance the tip of the cannula must penetrate before cerebral spinal fluid (CSF) is obtained as confirmation of subarachnoid placement.

It is a further object of this invention to facilitate easy and rapid backflow of CSF and therefore rapid confirmation of dural membrane puncture because of the large gauge of the introduced cannula.

It is a further object of this invention provide a cannula-obturator apparatus for introduction into the peridural tissues which minimizes tissue damage from the edges of the laterally placed cannula sideport by the use of a positive fitting obturator advanced flush to the surface of the cannula.

It is a further object of this invention to provide a cannula that upon penetrating into the subarachnoid space allows the safe placement of an indwelling catheter through such a cannula by minimizing shearing of said catheter as it is withdrawn or advanced through the sideport due to the presence of appropriately rounded sideport edges and an elliptically designed sideport opening.

It is an further object of this invention to provide a cannula that allows for the subarachnoid placement of catheters of sufficient diameter so as to overcome the disadvantages of small diameter subarachnoid catheters.

It is a further object of this invention to reduce the incidence of post dural puncture headaches by use of pencil point tip design of the cannula-obturator device.

It is a further object of this invention to facilitate easy, accurate and positive controlled direction and subsequent placement of the cannula-obturator device in the intravertebral space by use of a large gauge cannula (17-22 gauge) that resists the bending and deflection propensity of smaller gauge cannulas as they pass through and are repositioned in the tissues during the dural puncture procedure.

In accordance with the present invention, the above identified objects and others yet specified are achieve by a metal cannula-obdurator device of 18 to 22 external gauge with a solid point pencil tip geometry possessing a lumen running the longitudinal length of the cannula and which ends at the distal end of a cannula sideport located on the cannula tip. The end of the lumen forms an inclined wall which acts as a guide surface to direct a catheter advanced through the cannula lumen laterally and out the side port.

The present invention is introduced percutaneously most easily through an epidermal skin nick created by an 18-20 gauge sharp point beveled needle. The obturator-cannula device is advanced through the skin nick into the intervertebral space and penetrates the dural membrane in one motion (FIG. 5). The dura and intervening tissues between the subcutaneous layer and the dural membrane are penetrated by the cannula-obturator assembly with minimal damage due to 1) the pencil point tip design of the cannula, 2) the positive fitting obturator that maintains the cannula's smooth surface curve, and 3) the positive fitting obturator which obscures any cutting surface associated with the lateral side port opening. The obturator may be removed to assess for presence of cerebral spinal fluid (FIG. 5a) and replaced as needed for further positioning of the cannula. Because the lateral opening is so distally located on the cannula, the cannula-obturator apparatus can be advanced sparingly through the dural membrane until CSF backflow is obtained. Additionally, because the tip geometry of the cannula is less damaging to the dural membrane, a larger gauge cannula assembly can be used to penetrate the dura and permit easy and rapid backflow of CSF and thus unequivocal confirmation of dural puncture.

When it is confirmed that the tip of the cannula is in the subarachnoid space, a catheter may the threaded through the cannula as illustrated in FIG. 5b. Because an obturator is used in this device, identification of CSF is not prevented by accumulation of tissue debris in the cannula sideport: Patency of the opening is maintained and CSF return is unimpeded. When the catheter tip arrives at the end of the cannula, it is guided laterally and out the elliptical sideport by the cannula's internal channel guide surface. The angulation of the catheter as it exits the side port assures that it will not tend to curve back toward and penetrate the dural membrane. In addition, because a larger gauge catheter can be introduced, it will not tend to kink or knot when applied to the subarachnoid space.

The ellipse of the lateral opening of the present invention is much less radical than previous ground down lateral openings in cannula such as Witt's design. The sideport of the present invention more completely extends through and passed the dural membrane even after sparing penetration buy the cannula tip. A radically shaped ellipse with a long major axis as produced by grinding the lateral wall of the cannula can potentially allow CSF backflow while a significant portion of the lateral opening is contiguous with and/or inside the dural membrane. The operator then has the choice of accepting backflow as a positive indicator, or must further advance the tip of the cannula to assure the opening is not obstructed by the dural membrane. In the former case, a catheter could be threaded through the opening and rent the dura, or be deflected in an unanticipated direction. In the latter case, the operator may risk penetration of subdural structures by the cannula tip upon further advancement of the needle. Both possibilities are undesirable complications.

Upon insertion/placement of the catheter through the present invention, the cannula may be removed without danger of shearing the tip of the catheter on the lateral opening's bordering edge. The linear measure of the major axis of the lateral opening is equal to the outer diameter of the cannula. The minor axis of the elliptical orifice is not more than 0.82 and not less than 0.76 times the major axis in linear dimension: This imparts a true elliptical geometry to the lateral opening. Preserving the elliptical nature of the opening itself prevents catheter shear. Witt's design (U.S. Pat. No. 4,842,585) provides for an elongated slot-like opening (column 4 line 19) where the minor axis of the lateral opening is approximately 0.375 of the major axis. When a catheter is advanced or withdrawn through the orifice, the slot-like design allows excessive movement of a catheter up and down the major axis of the opening and against the circumferential border edge of the orifice. The elliptical, as opposed to the elongated slot-like, configuration minimizes pinching of the catheter by the right and left lateral border edges of the orifice. Since the minor axis determines the maximum diameter of catheter that will pass through the lateral opening, an elongated opening presents relatively straight right and left lateral edge against which a moving catheter can bind. An elliptical shaped orifice presents right and left lateral surfaces which are curved and consequently will not bind a catheter moved through the orifice. Thus, an advantage of present invention is to deter catheter shearing upon its advance or withdrawal through the lateral opening. This is accomplished by providing an orifice of elliptical shape, by the rounded and polished machining of the opening's entire circumferential edge, and the ability to use large gauge thick walled catheters.

BRIEF DESCRIPTION OF THE DRAWINGS

An embodiment of the invention will be explained hereunder in more detail with reference to the drawings in which, FIG. 1 Illustrates an isometric representation of the cannula-obturator assembly.

FIGS. 2a, 2b and 2c respectively illustrate the cannula-obturator device by surface front view, sectioned side view and sectioned front view.

DESCRIPTION OF THE PREFERRED EMBODIMENTS

Figure 1:
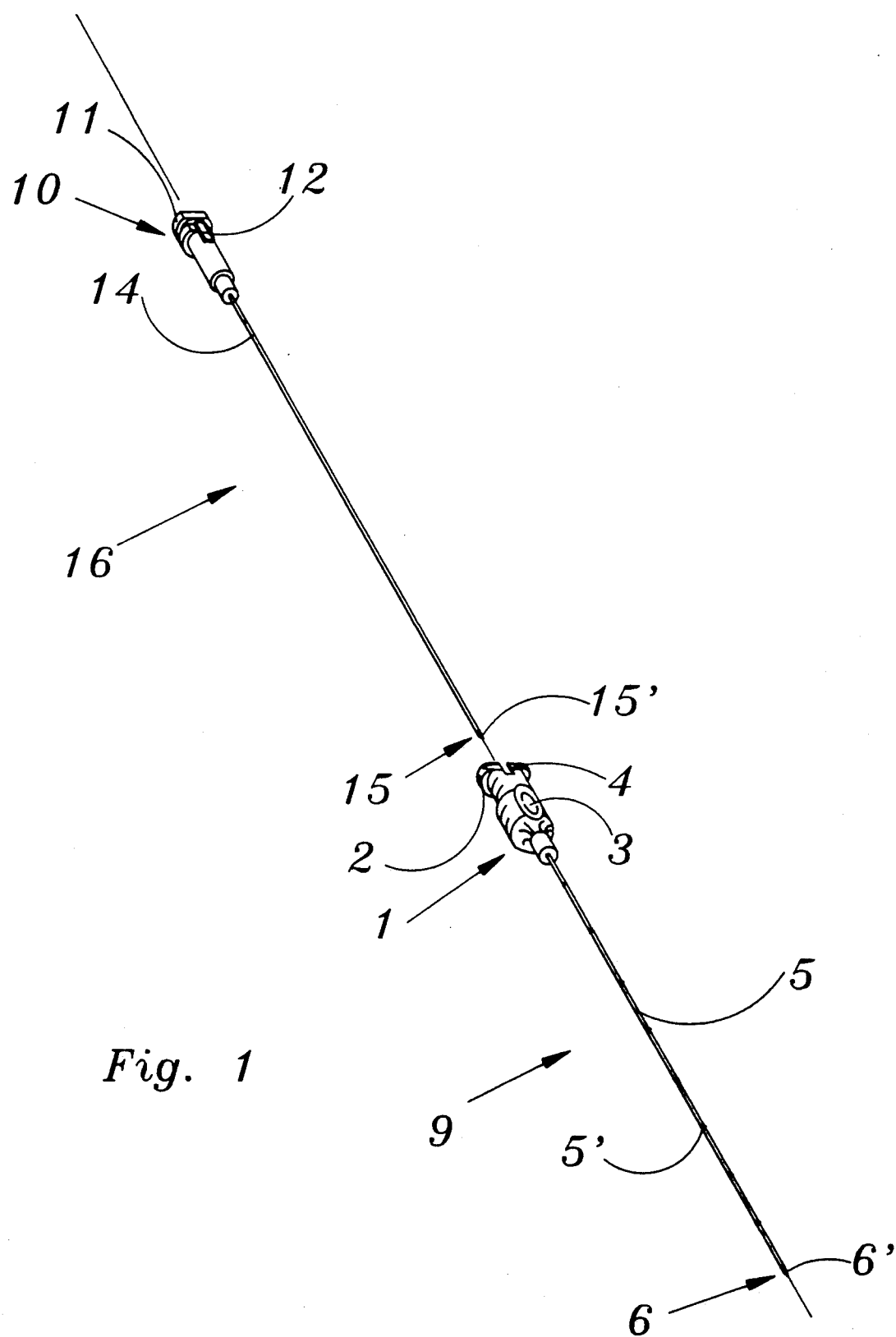
Figure 2:
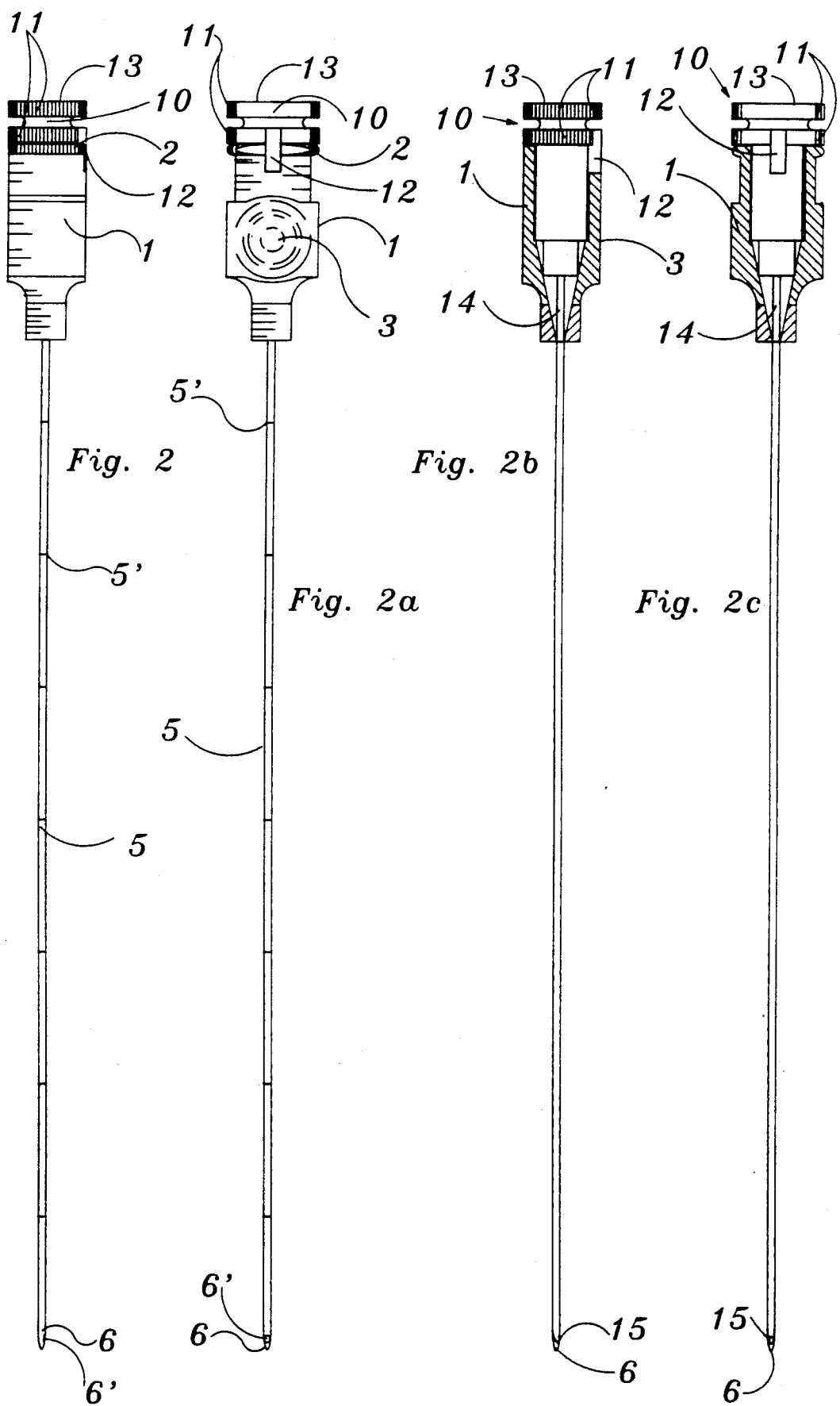
FIG. 2 Illustrates the cannula-obturator device in its entirety with a surface side view.
Figure 3:
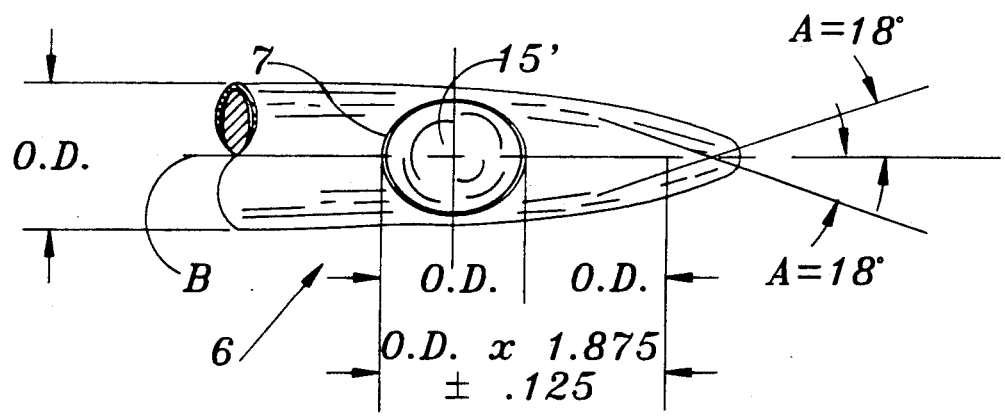
FIG. 3 Illustrates the tip of the cannula with the obturator inserted by surface top view.
Figure 3A:
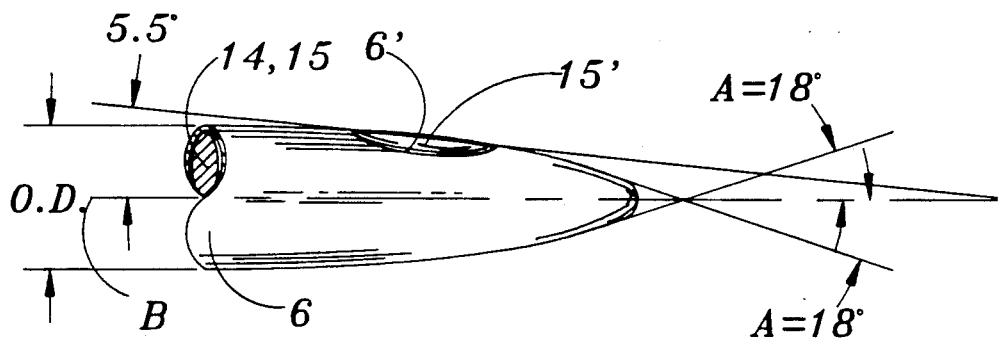
FIG. 3a Illustrates the tip of the cannula with obturator inserted by a surface side view.
Figure 3B:
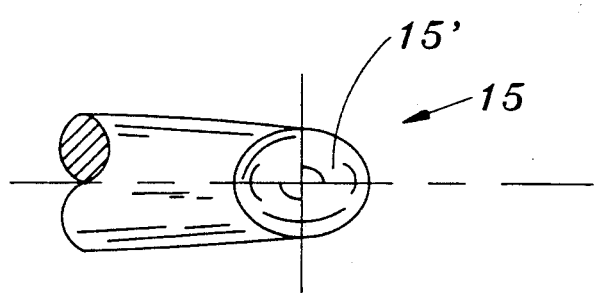
FIGS. 3b and 3c respectively illustrate the tip of obturator by surface top view and by surface side view.
Figure 3C:
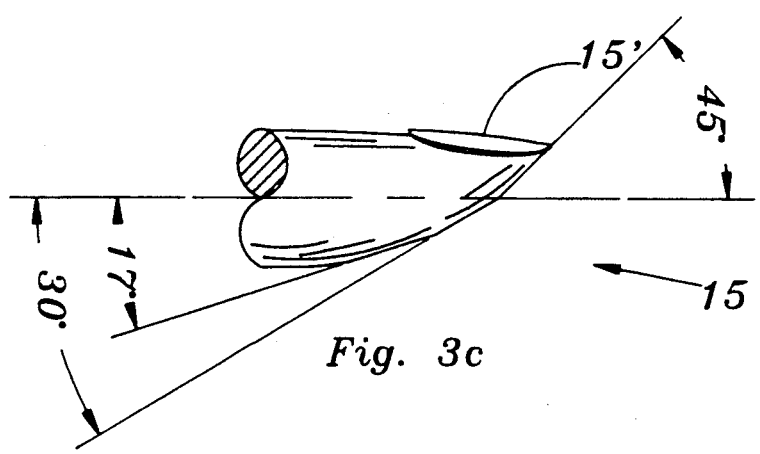
Figure 4:
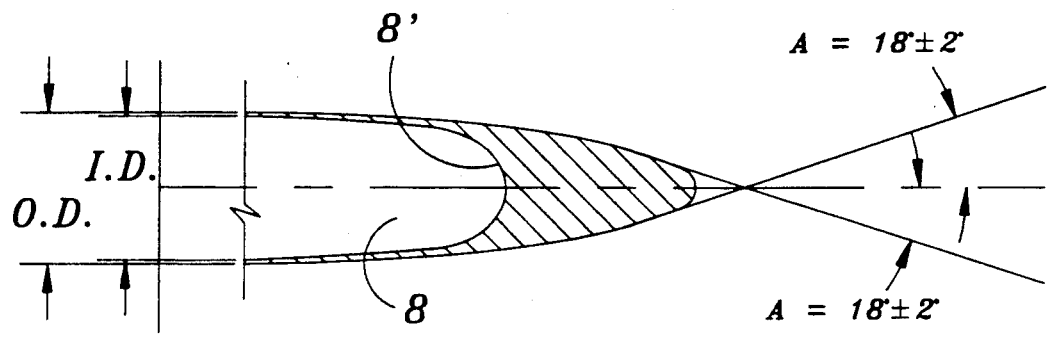
FIG. 4 Illustrates the tip of the cannula by sectioned top view.
Figure 4A:
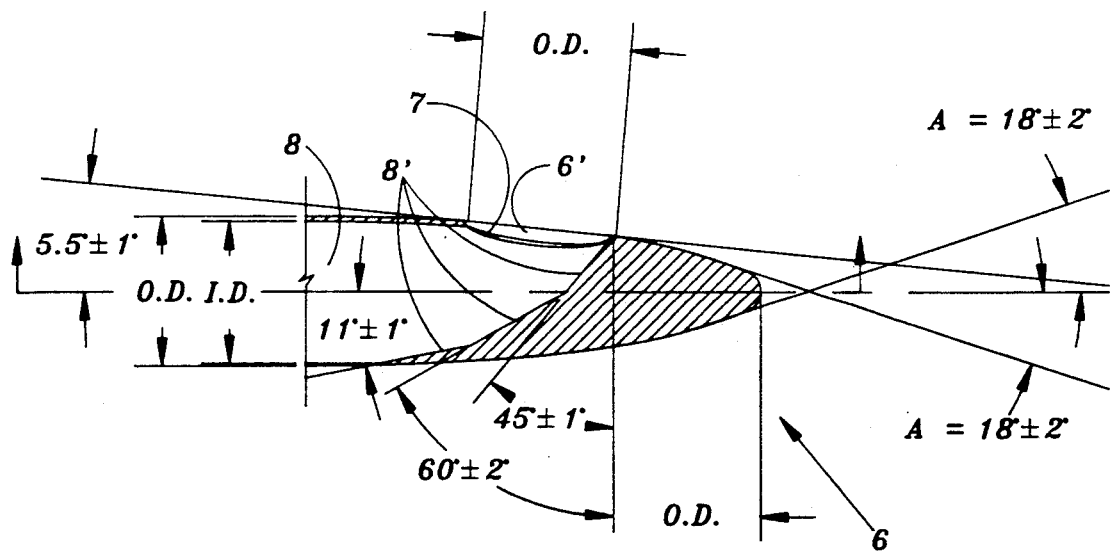
FIG. 4a Illustrates the tip of the cannula by sectioned side view.

The following detailed description is of the best presently contemplated mode of carrying out the invention. This description is not to be taken in a limiting sense, but is made merely for the purpose of illustrating the general principle of the invention. The scope of the invention is defined by the appended claims.

The embodiment of the invention chosen for the purpose of illustration is a cannula device 9 comprised of a hollow metal catheter assembly 3 with a hub 1 and tip 6 and an obturator assembly 16 with a hub 10, a solid metal shaft 14 and a tip 15. The needle shaft has an interior central passage or channel 8. The hub of the cannula 1 and the hub of the obturator 10 are crimped to the front end of their respective shaft. The end of the cannula shaft 5 terminates in a solid closed blunt tip 6.

The end of the obturator shaft 15 terminates in an inclined surface 15' of matched contour to the hollow channel terminus 8'. One needle shaft outer diameter (O.D.) length from the end of the cannula tip 6 and located on the lateral surface of the tip 6 is a true elliptical opening 6'. More specifically, the illustrated metal cannula 9 comprises an elongated straight tube 5 whose front end is closed by a rotationally symmetric tapered tip 6 formed integrally with cannula 5. The tip 6 is that part of the distal cannula which departs from the straight cylindrical surface of the shaft and terminates in a pencil point. The tip 6 includes a lateral opening (sideport) 6' on its angled/curved surface: The tip originates its curved surface at the proximal edge of this lateral opening. The tip 6 is not more than 2 (two) times and not less than 1.75 (one and three-fourths) times the outer diameter of the cannula in length (thus, for an O.D. of 0.0216 inch, the maximum length of the tip would be 0.0432 inch). The entire external surface of the tip 6 including the lateral opening 6' is rotationally symmetric and conical, and smoothly transitions from the distal portion of the cannula shaft's 5 external surface.

The metal hub 1 is funnel shaped internally to easily facilitate insertion of the obturator or catheter. The hub 1 is designed to accommodate either leur-slip or leur-lock syringes. The external surface of the hub 1 is designed with a flat machined top and bottom surface 3 which provide an area for a needle gauge stamp. The flattened surfaces provide the operator with visual and tactile appreciation of the orientation of the lateral opening 6', a grasping surface and visual identification of the needle gauge size. The gauge stamp also provides ready identification of needle size to facilitate reassembly with its proper sized obturator. The curved lateral surfaces of the hub 1 are scored with finger grooves 2 to provide a positive grasping surface should the operator change finger position during application of the cannula-obturator assembly. Both design features provide a positive grasping surface to aid in the ease and accuracy of cannula-obturator application by the operator. The hub 1 is also provided with a positive locking groove 4 that accepts the obturator locking tab 12 thereby providing a positive fit of the obturator into the hollow channel 8. The groove 4 and tab 12 mechanism also facilitate appropriate orientation of the obturator in the hollow cannula. The hub 1 of the cannula assembly 9 is crimp fitted onto the cannula shaft 5. The metal shaft of the cannula 5 is penetrated by a hollow channel 8 extending from the metal hub 1 to the solid metal tip 6. The external surface of the shaft 5 is marked from the distal tip at 1 (one) centimeter intervals 5' up to the hub 1. The markings are made in such a manner as to retain the smooth surface integrity of the external surface of the shaft thereby preventing drag on the cannula surface as it passes through the tissues during application. The shaft terminates in a tip 6 which has both a solid component and a lateral opening 6'.

The hub 10 of the obturator assembly 16 is crimp fitted onto the obturator shaft 14. The obturator hub 10 positively fits into the cannula hub 1. The top surface of the obturator 13 is machined flat to provide a gauge stamp area facilitating easy and accurate reassembly of like sized obturator and cannulas. Finger grooves 11 are scored into the two collar surfaces of the obturator hub 10 to 25 provide a positive grasping surface for application of the obturator assembly 16 to the cannula assembly 9. The obturator shaft 14 is a solid metal rod extending from the end of the obturator hub 10 and terminating in a inclined tip 15. The outer diameter of the obturator shaft 14 is slightly smaller than the internal diameter of the hollow channel of the cannula 8 so that it easily passes through the hollow channel but yet occludes passage of liquid material through the hollow channel. The obturator assembly 16 provides added axial strength to the cannula to help it resist bending during application thereby facilitating accurate placement. The tip of the obturator 15 is machined so that it inclines 15' in like manner and conforming with 5 the internal guiding surface of the hollow channel 8'. Also, the tip of the obturator 15 positively fits flush with the curved external tip surface at the lateral opening 6' of the cannula tip 6. This preserves the curvature of the cannula tip 6, overcomes the potential cutting action of the sideport edge 7, and prevents occulusion of the hollow channel 8 by extraneous material as the cannula-obturator assembly is advanced or withdrawn during application. The fit of the obturator tip 15 at the lateral opening 6' is facilitated by the fact that said lateral opening is bored rather than ground down into the lateral wall of the cannula shaft.

The hollow channel 8 of the metal cannula is bored by laser or mechanical machining to a point terminating at a line drawn from the center of the lateral opening 6 which perpendicularly intersects the mid-axial line of the shaft 8. This process establishes the hollow channel 8 completely to the proximal boarder of the lateral opening 6 and partially to the center of the lateral opening 6. This process also establishes part of the inclined surface of the of the hollow channel at the cannula tip 8'. The elliptical lateral opening 6' is established by a drill or laser burn angled not more than 85 degrees and not less than 83 degrees from the point of tangency from the center point of the orifice toward the longitudinal center line of the cannula shaft. This burning or drilling process is continued to a depth into the underlying cannula of not greater than $\frac{1}{3}$rd the distance of tip diameter at that point. This laser or drilling process establishes the elliptical lateral opening 6', partially completes the most distal portion of the hollow channel 8, and partially establishes the inclined surface 8' of hollow channel 5 at the tip 6. The inclined channel 8' allows the similarly angled obdurator tip 15' to be positively guided into its position to occlude the lateral opening 6 and therein accommodates a positive fit of the elliptically tipped 15' obturator 15 at the elliptically shaped sideport 6'. The inclined surface 8' of the hollow channel 8 at the needle tip 6 also acts as a positive guiding surface for a catheter introduced through the hollow channel 8 and advanced laterally out through the cannula sideport 6'. The portion of the tip 6 distal to the sideport 6' is of solid metal construction. The internal edge 8' of the solid portion of the cannula metal tip 6 is delimited by the inclined surface of the hollow channel 8'. The sideport 6' has a common curved edge from the interior wall surface to the exterior wall surface. The angle of the major inclined surface A of the tip 6 forward from the distal edge of the lateral opening 8' is measured by a line drawn tangent to the midpoint of that major inclined surface A and intersecting the longitudinal center line of the cannula shaft 5. This angle is at least 15 degrees but not more than 20 degrees. The angle of inclination B of the major axis of the elliptical lateral opening 6' in relation to the longitudinal axis of the cannula shaft 5 is not less than 4.5 and not more than 6.0 degrees with 5.5 degrees being nominal. The elliptical lateral opening or sideport 6' is provided as part of the cannula tip 6 in that it is located on the inclined surface of the cannula tip 6. This positioning allows the orifice 6' to be more roundly elliptical in geometry than if the lateral opening were placed on the wall of the shaft. The linear measure of the major axis of the lateral opening 6' is equal to the O.D. of the needle cannula; the minor axis of the elliptical orifice 6' is not more than 0.82 and not less than 0.76 times the major axis in linear dimension. This imparts a true elliptical geometry to the lateral opening 6'. Preserving the elliptical shape of the orifice 6' presents right and left lateral surfaces which are curved and will not bind a catheter as it moves through the orifice 6'. The distance from the most distal edge of the lateral opening 6' to the end of the tip 6 is not more than the O.D. of the cannula shaft 5. Thus, the total distance of the cannula tip 6 equals the major axis of the elliptical lateral 5 opening 6' plus the distance from the most distal edge of the lateral opening 6' to the tip end 6: this sum is not greater than two times the O.D. of the needle shaft.

The lateral opening (sideport) 6' directly communicates with the cannula's hollow internal channel 8 as previously described. The sideport 6' is bored or drilled by laser or mechanical machining rather than ground into cannula side wall. The edges 7 of the sideport 6' are honed and polished or burnished. This provides subtle roundness to the sideport edge 7 as well as causing the edge to be slightly receded below the external surface of the tip 6. Combined with the elliptical shape of the lateral opening 6', these features act to reduce the cutting nature of the sideport edges 7 and effectively prevent damage to tissues penetrated by the cannula-obturator device 17 as well as prevent shearing of a catheter 19 advanced or withdrawn through the sideport 6'. The placement of the sideport 6' on the angled surface of the cannula tip 6 rather than the parallel lateral wall of the cannula shaft 5 combined with the inclined internal guide surface 8' of the cannula lumen 8 allows the direction of a catheter 19 inserted into the lumen 8 from the cannula hub 1 to exit the sideport 6' in a controlled direction away from the penetrated dural membrane 24.

Figure 5:
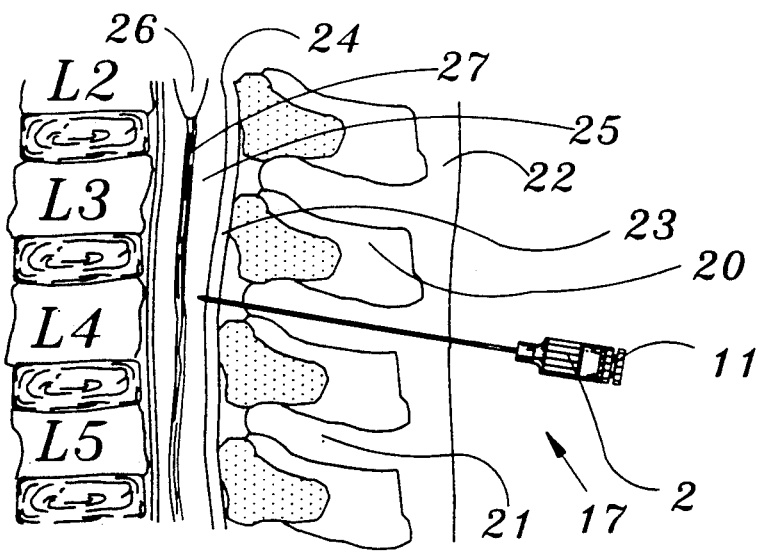
FIG. 5 Illustrates the cannula-obturator device in application 10 with representative anatomical drawings showing the cannula-obturator device applied in the subarachnoid space.
Figure 5A:
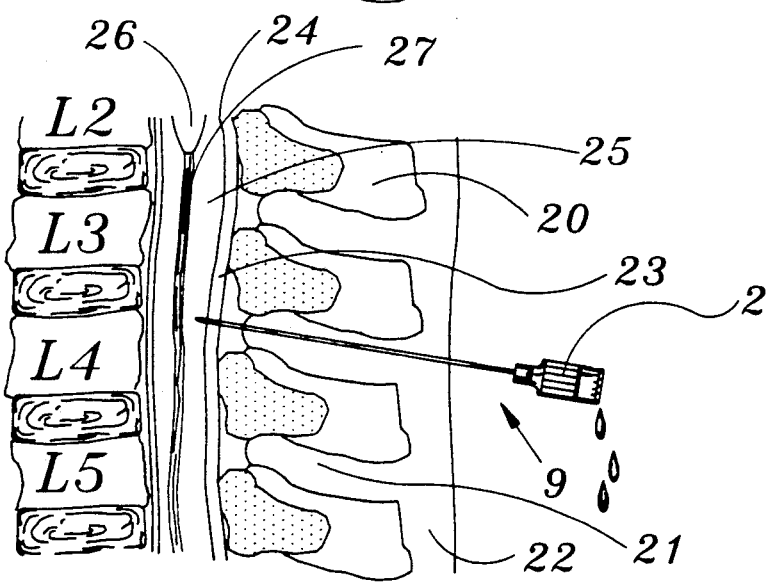
FIG. 5a Illustrates the cannula in the subarachnoid space with the obturator removed, and CSF exiting the hub opening.
Figure 5B:
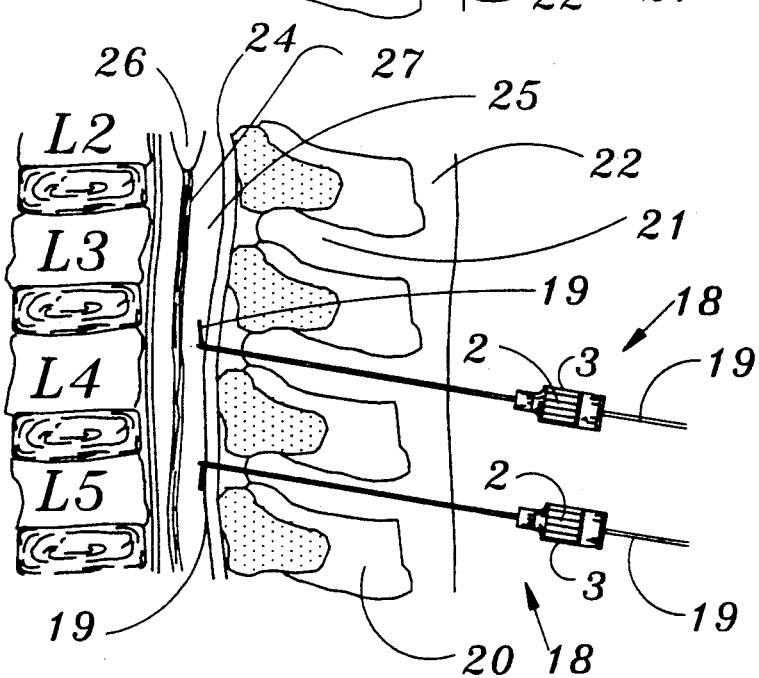
FIG. 5b Illustrates the cannula in the subarachnoid space with a catheter threaded from the hub end of the cannula exiting the lateral opening of the cannula into the subarachnoid space.
Figure 6:
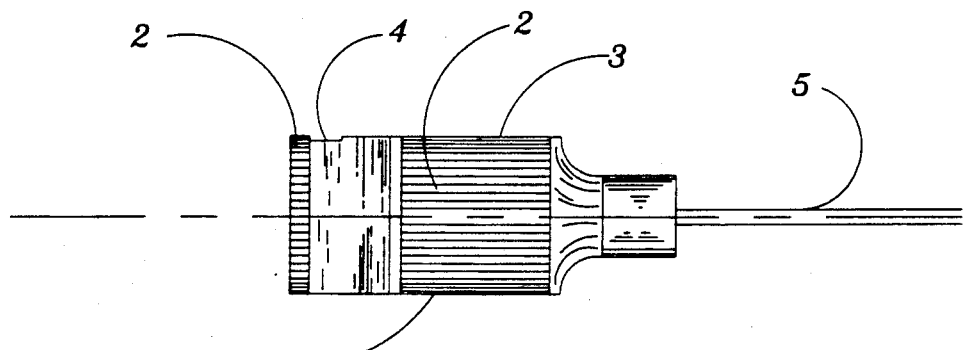
FIG. 6 Illustrates the cannula hub surface by a front view.
Figure 6A:
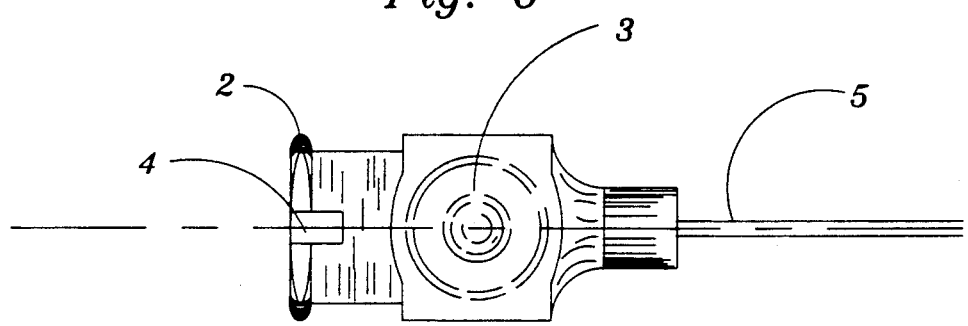
FIGS. 6a, 6b and 6c respectively illustrate the cannula hub by surface side view, by sectioned front view and by sectioned side view.
Figure 6B:
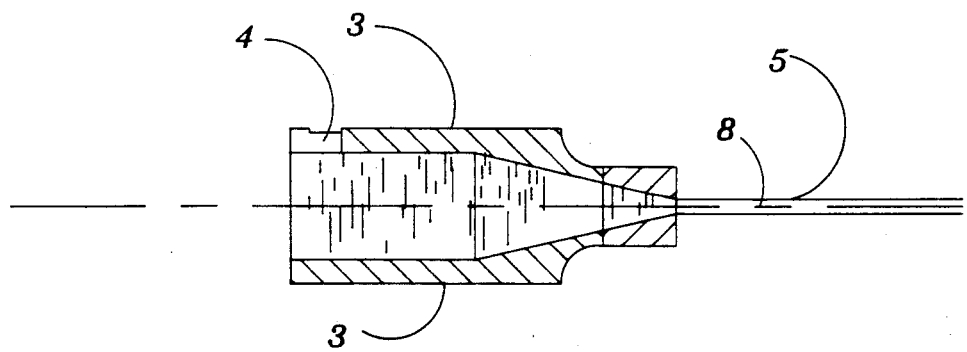
Figure 6C:
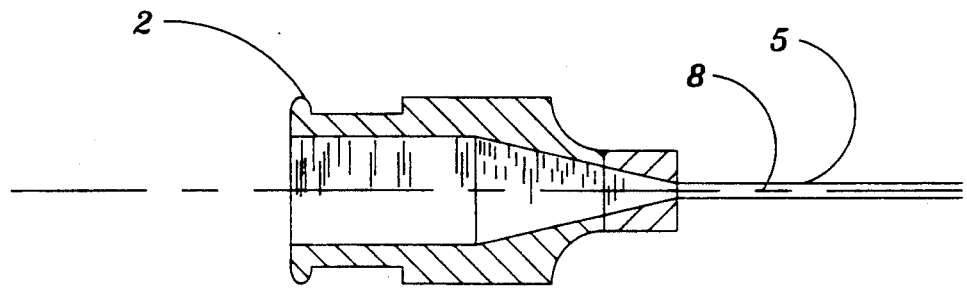

The application of the cannula-obturator 17 device is described with reference to FIGS. 5, 5a, 5b. First, the skin of the lumbar area of the back is prepared with antiseptic solution and draped in a sterile fashion. The vertebral spinous processes 20 are palpated to identify the intervertebral spaces 21. Classically, the L3-4, L4-5 and occasionally L5-S1 intervertebral spaces are used to access the underlying subarachnoid space 23. When the dura 24 is punctured below the L2 vertebral body, the spinal cord 26 is not endangered by needle trauma. At the L2 vertebral level, the spinal cord terminates and the lumbar and sacral nerve roots approximate form the cauda equina 27.

After the desired intervertebral space 21 has been identified, the operator may apply a subcutaneous skin wheal of local anesthetic followed by injection of additional local anesthetic more deeply into the tissue layers of the back 22. The operator then uses a sharp point beveled needle (preferably 18 guage) to pierce the skin so as to create a small nick through which the cannula-obturator device 17 may then be easily introduced and advanced.

The cannula-obturator device 17 is introduced through the overlying skin of the intervertebral space 21 typically via a midline approach. The angle of the midline approach usually slightly departs from the surface of the patient's back so that the tip 6 and 15' of the cannula-obturator 17 is directed slightly cephalad as illustrated in FIG. 5. Using the thumb and forefinger, the dominant hand is applied to the cannula-obturator hub 1 and 10. The operator grasps the hub 1 on the flat surface 3 and prepares for insertion of the cannula-obturator tip 6 and 15' into the skin nick by stabilizing the dominant hand against the patient's back using that hand's 3rd and 4th digits. The opposite hand is then also stabilized against the patient's back and the operator proceeds to grasp the shaft 5 of cannula-obturator device 17 with thumb and forefinger. The cannula-obturator device 17 is advanced under positive control in one forward motion at an angle slightly departed from the perpendicular surface of the skin passing through the skin nick, subcutaneous layers and ligaments of the spine 22 and through the intervertebral space 21 ultimately piercing the dural membrane 24. The operator then extracts the obturator 16 from the cannula 9 to assess the backflow of cerebral spinal fluid (CSF). Presence of CSF that the cannula's lateral opening 6' is in the subarachnoid space 25. The obturator 16 may be reinserted into the cannula 9 so that in the event there is no CSF backflow, the cannula-obturator device 17 may be advanced or repositioned until backflow is obtained. The lineally placed markings on the shaft of the cannula 5' are utilized to assess the depth of tip 6 insertion: typically, the depth of the dural 5 membrane from the surface of the skin is approximately 4 centimeters.

The operator then identifies the orientation of the lateral opening 6' by visually identifying the locking tab 12-locking grove 4 assembly on the cannula-obturator hub. The operator then affirms that the lateral opening 6' is oriented either cephalad or caudad as desired in preparation for introduction of the catheter 19 through the hollow channel 8 of the cannula and its eventual advancement out the lateral opening 6' of the cannula tip 6.

The operator may inject suitable medications into the subarachnoid space 25, or thread a suitably pliable and appropriately sized catheter 19 into the cannula hub 1 advancing it through the hollow channel 8. The catheter tip is guided out the lateral opening 6' by the inclined ascending guiding surface 8' of the channel wall. The catheter 19 emerges out the lateral opening 6' into the subarachnoid space 25 at an angle. The catheter 19 only need be advanced a distance of 2 centimeters into the subarachnoid space 25. As illustrated by FIG. 5b, the location of the sideport 6' on the curved surface of the cannula tip 6 allows the catheter 19 to be directed away from the dural membrane 24 with certainty. Thus as the catheter 19 exits the lateral opening 6', piercing or renting of the dural membrane 24 by the catheter 19 is precluded. Additionally, as the catheter 19 is advanced into the subarachnoid space 25 at an obligatory angle, the catheter 19 is deterred from piercing underlying structures since the catheter tip 6 is caused to be deflected off any structures it may encounter.

When the operator has confirmed that the catheter 19 has been introduced the appropriate distance into the subarachnoid space 24, catheter 19 placement can be confirmed by aspiration of CSF from the catheter 19 before removal of the cannula 9. When catheter 19 placement is positively confirmed, the cannula 9 is removed by withdrawing it backwards over the inserted catheter 19 while simultaneously providing gentle forward pressure on the catheter 19 with the opposite hand.

The operator then reassess the appropriate depth of catheter placement and patency of the indwelling catheter before fixing the catheter to the patient's skin by tape or other means. Thereafter, anesthetic or analgesic preparations suitable for introduction into the subarachnoid space may be injected through the catheter. Thus, a pliable catheter remains as the only indwelling appliance.

We claim:

1. A cannula-obturator device for placement of an indwelling catheter and for providing spinal anesthesia therethrough comprising:

a cannula comprising an axial shaft and terminating in a curved pencil point tip geometry, the cannula having a hollow channel extending through the center of the shaft from a hub at the front end to its termination communicating with an elliptical lateral opening on the curved surface of the tip end;

a hollow channel at the tip end conforming to an inner curved wall surface ascending obliquely up from the bottom of the channel to the distal end of an elliptical lateral opening located on the curved surface of the cannula tip which provides both a guide surface for direction of a catheter to exit the lateral opening and occludes the tip distal to the end edge of the elliptical lateral opening;

a tip having a pencil point geometry and includes an elliptical lateral opening entirely located on and conforming to the tip's curved surface wherein the piercing portion of said tip distal to the end edge of the elliptical lateral opening is of solid metal;

an obturator comprising a solid rod comprising an axial shaft extending from a hub at the front end to the termination of the rod at the tip end said shaft having an external diameter smaller than the internal diameter of said hollow channel allowing the rod to slide into said hollow channel such that the tip of the rod positively but temporarily is received at said lateral opening of the said cannula so that the lateral opening and tip of the solid rod when positively fit together define an unbroken curved surface of said cannula tip which conforms to the inclined surface geometry of the cannula tip;

an elliptical lateral opening, having a front and an end edge, on the tip of said cannula providing communication to the front end of the cannula for cerebral spinal fluid when said solid rod is withdrawn from the axial channel of the cannula.

2. The cannula of claim 1, wherein an elliptical lateral opening in the curved surface of the cannula tip is established by boring or drilling so that the location of said lateral opening's end edge from the terminus of the tip is equal to the outer diameter of the said cannula and wherein the entire circumferential edge of said lateral opening is machine rounded from the exterior surface to the interior surface and wherein the major axis is equal to the outer diameter of the cannula shaft and the minor axis of the lateral opening is 0.82 to 0.76 (inclusive) times the major axis lineal length;

3. A cannula obturator device defined in claim 1 wherein a cannula shaft is marked at lineally spaced increments on the exterior surface at intervals of every 1 (one) centimeter beginning from the cannula tip and extending to the end of the hub.

4. A cannula-obturator device defined in claim 1, wherein the angle of the pencil point tip's major curved-/inclined surface is defined by a line tangent to the curved surface intersecting the longitudinal center line of the cannula shaft at an angle of 15 to 20 degrees.

5. A cannula-obturator device defined in claim 1, wherein the pencil point tip begins from the point the exterior cannula shaft surface departs from a line parallel to the longitudinal axis of the cannula shaft providing a tip length that is 1.75 to 2.0 (inclusive) times as long as the outside diameter of the cannula shaft.

6. A cannula-obturator device defined in claim 1 having an obturator temporarily placed in the channel of the cannula during application of the cannula to the subarachnoid space further comprising;

an obturator tip designed with an elliptic end conforming to the shape of the elliptic lateral opening and is positively received at said lateral opening of the cannula;

an obturator tip which occludes said lateral opening;

an obturator tip machined with a surface which positively fits at said lateral opening and lays flush with the curved surface of the cannula tip;

an obdurator with a hub crimped into its front end opposite the tip end and which is positively received into the hub of said cannula.

7. A cannula-obturator device of claim 1 further having a hub designed for attachment of a syringe to the cannula.

* * * * *